(12) United States Patent
De Troostembergh et al.

(10) Patent No.: US 7,091,013 B2
(45) Date of Patent: Aug. 15, 2006

(54) PROCESS FOR THE MANUFACTURE OF 2-KETO-L-GULONIC ACID

(75) Inventors: Jean-Claude Marie-Pierre Ghislain De Troostembergh, Houwaart (BE); Ignace André Debonne, Vollezele (BE); Willy Richard Obyn, Kampenhout (BE); Catherine Gwenaëlle Michelle Peuzet, Bruxelles-Schaerbeek (BE)

(73) Assignee: Cerestar Holding B.V., Sans Van Gent (NL)

( * ) Notice: Subject to any disclaimer, the term of this patent is extended or adjusted under 35 U.S.C. 154(b) by 0 days.

(21) Appl. No.: 10/486,969

(22) PCT Filed: Aug. 2, 2002

(86) PCT No.: PCT/EP02/08623

§ 371 (c)(1),
(2), (4) Date: Sep. 29, 2004

(87) PCT Pub. No.: WO03/016508

PCT Pub. Date: Feb. 27, 2003

(65) Prior Publication Data

US 2005/0019881 A1 Jan. 27, 2005

(30) Foreign Application Priority Data

Aug. 15, 2001 (GB) .................................. 0119864.7

(51) Int. Cl.
*C12P 7/60* (2006.01)
*C12N 1/20* (2006.01)

(52) U.S. Cl. .................. 435/138; 435/41; 435/132; 435/252.1; 435/252.5

(58) Field of Classification Search .................. 435/41, 435/42, 138, 822, 823, 834
See application file for complete search history.

(56) References Cited

U.S. PATENT DOCUMENTS

| 3,234,105 | A | * | 2/1966 | Motizuki et al. ........... 435/138 |
| 4,935,359 | A | | 6/1990 | Yin et al. |
| 5,312,741 | A | * | 5/1994 | Hoshino et al. .............. 435/42 |
| 6,387,654 | B1 | * | 5/2002 | Liaw et al. .................... 435/42 |

FOREIGN PATENT DOCUMENTS

| CN | 1360024 A | 7/2002 |
| EP | 0 278 447 A2 | 8/1988 |
| EP | 0 359 645 A1 | 3/1990 |
| EP | 0 805 210 A2 | 4/1997 |
| EP | 0 805 210 A3 | 4/1997 |
| FR | 1376741 | 2/1965 |
| WO | WO 01/09152 A1 | 2/2001 |

OTHER PUBLICATIONS

Todar, K. 2003. Todar's Online Textbook of Bacteriology: The Genus Bacillus. http://textbookofbacteriology.net/Bacillus.html.*

Yuan et al., "Coimmobilization of *Gluconobacter oxydans* and *Bacillus cereus* for Bioconversion of 2-Keto-L-gulonic Acid," Annals New York Academy of Sciences, pp. 628-633—Document No. XP008019736, no pub year.

Urbance et al., "Taxonomic Characterization of Ketogulonigenium Vulgare Gen. Nov., Sp. Nov. And Ketogulonigenium Robustum Sp. Nov., Which Oxidize L-Sorbose to 2-Keto-L-Gulonic Acid," International Journal of Systematic and Evolutionary Microbiology, vol. 51, pp. 1059-1070 (2001).

* cited by examiner

*Primary Examiner*—Sandra E. Saucier
*Assistant Examiner*—Lora E Barnhart
(74) *Attorney, Agent, or Firm*—Fitch, Even, Tabin & Flannery

(57) ABSTRACT

The present invention discloses a process for producing sodium 2-keto-L-gulonate from sorbitol and recovering 2-keto-L-gulonic acid in high recovery yields, by controlled cation exchange treatment of the micro-organism free fermentation broth and/or adjusting PH of said purified fermentation broth, followed by direct crystallisation of 2-keto-L-gulonic acid monohydrate.

12 Claims, No Drawings

PROCESS FOR THE MANUFACTURE OF 2-KETO-L-GULONIC ACID

This application is the U.S. National Stage of International Application PCT/EP02/08623, filed Aug. 2, 2002, the complete disclosure of which is incorporated herein by reference, and which was published under PCT Article 21(2) in English. The complete disclosures of the deposits numbered LMG-20356, and LMG-P20355 with BCCM/LMG are incorporated herein by reference.

TECHNICAL FIELD

The present invention relates to a process for producing sodium 2-keto-L-gulonate and recovering 2-keto-L-gulonic acid monohydrate in high recovery yields

BACKGROUND OF THE INVENTION

It is known that 2-keto-L-gulonic acid can be produced by fermentation from L-sorbose and/or sorbitol.

FR 1 376 741 relates to a process for the preparation of 2-keto-L-gulonic acid, which is an intermediate in the production of L-ascorbic acid (=vitamin C).

It is demonstrated that the fermentative mixture can be used directly for esterification of 2-keto-L-gulonic acid into L-ascorbic acid.

EP 0 518 136 describes a method for preparing 2-keto-L-gulonic acid that comprises cultivating a mixed culture of micro-organism (A) which belongs to the genus *Gluconobacter* or *Acetobacter*, and a micro-organism (B) capable of producing 2-keto-L-gulonic acid from L-sorbose and both of said micro-organisms are co-existing in the medium during at least part of the entire cultivation period.

EP 0 278 447 relates to a fermentation process for producing 2-keto-L-gulonic acid by conversion of L-sorbose by means of mixed cultures of microorganisms comprising *Gluconobacter oxydans* and *Bacillus megaterium*.

EP 0 972 843 relates to a continuous fermentation process for the manufacture of 2-keto-L-gulonic acid from sorbitol by fermentation with micro-organisms, in which process a nutrient medium containing sorbitol is incubated in a first fermentation vessel with a micro-organism capable of converting sorbitol to L-sorbose, and the resulting fermentation broth is transferred continuously to a second fermentation vessel where it is incubated with a micro-organism capable of converting L-sorbose to 2-keto-L-gulonic acid.

EP 0 213 591 describes a process for producing 2-keto-L-gulonic acid and vitamin C respectively and the method further describes that the isolation of 2-keto-L-gulonic acid may be effected by the formation of a salt or by using the difference in properties between the product and impurities such as solubility, adsorbability and distribution coefficient between two solvents. Although the use of an adsorbent such as ion exchange resins is described as being one of the most convenient processes for isolation of the product, the 2-keto-L-gulonic acid thus obtained is in general not pure.

EP 0 221 707 relates to a method for producing 2-keto-L-gulonic acid and describes a harvesting method wherein the culture broth is freed of cells by filtration, centrifugation or treatment with activated carbon and concentration of the solution. Solvent extraction, chromatography, precipitation or salting-out may be applied in a suitable combination and/or in repitition.

WO 01/09152 relates to a process for the purification of 2-keto-L-gulonic acid by continuous liquid chromatography using a weakly basic ion exchange resin. It mainly relates to recovering 2-keto-L-gulonic acid substantially water-free from aqueous solutions.

EP 0 359 645 relates to a process for obtaining pure 2-keto-L-gulonic acid from a fermentation broth containing the calcium salt of 2-keto-L-gulonic acid. Said process comprises separating the insolubles, concentrating the medium, precipitating calcium sulphate by adding concentrated sulphuric acid, treating with cation exchange resin, removing strong acid ions by anion exchanger, concentration and separating the 2-keto-L-gulonic acid by crystallisation.

EP 0 805 210 relates to a process wherein sodium 2-keto-L-gulonate is crystallised from the fermentation broth, the obtained crystals are pulverised and suspended in a lower alcohol containing a water-free acid and finally the salt of 2-keto-L-gulonate is converted into a lower alkyl ester of 2-keto-L-gulonic acid.

A further need exists to have a process for obtaining 2-keto-L-gulonic acid in high recovery yields and wherein the purification step is simple and easily reproducible.

The current invention provides such a process.

SUMMARY OF THE INVENTION

The present invention discloses a process for producing sodium 2-keto-L-gulonate by fermentation and recovering 2-keto-L-gulonic acid monohydrate crystals and said process comprises the following steps:

a) Fermentatively converting sorbitol into at least 50 g/L sodium 2-keto-L-gulonate, b) removing the micro-organisms from the fermentation medium thereby obtaining a micro-organism-reduced fermentation broth, preferably micro-organism-free fermentation broth, c) converting sodium 2-keto-L-gulonate into 2-keto-L-gulonic acid in the micro-organism-reduced fermentation broth, and removing proteins to a concentration below 2400 ppm (measured as nitrogen on dry substance) for obtaining a purified fermentation broth, and/or adjusting pH of purified fermentation broth for avoiding the formation of vitamin C in a concentration higher than 3% (based on dry substance) during the subsequent evaporation of water, d) evaporating water from the purified fermentation broth for obtaining a concentrated purified fermentation broth, and e) recovering 2-keto-L-gulonic acid monohydrate crystals by crystallisation from the concentrated purified fermentation broth with a recovery yield for 2-keto-L-gulonic acid of 80% or higher.

The current invention further relates to a process wherein in said process the conversion into 2-keto-L-gulonic acid and the removal of proteins is effected by ion exchange treatment consisting of cation exchange resin.

Furthermore, the current invention relates to a process comprising the following steps:

a) Preparing a fermentation culture medium containing a nitrogen-source and as carbon-source sorbitol, b) Inoculating the fermentation culture medium with micro-organisms for converting sorbitol into L-sorbose, c) Allowing the micro-organisms to grow until at least 100 g/L L-sorbose is obtained in the fermentation medium, d) Terminating the conversion of sorbitol into L-sorbose, e) Inoculating the fermentation culture medium with a mixed culture of micro-organisms for converting L-sorbose into sodium 2-keto-L-gulonate, f) Allowing the micro-organisms to grow until at least 50 g/L sodium 2-keto-L-gulonate is obtained in the fermentation medium, g) removing the micro-organisms from the fermentation medium by filtration for obtaining a micro-organism-reduced fermentation broth, preferably micro organism-free fermentation broth, h) converting with cation exchange resin sodium 2-keto-L-gulonate into 2-keto-L-gulonic acid in the micro-organism reduced fermentation broth, and removing proteins to a concentration below 2000 ppm proteins (measured as nitrogen on dry substance) for obtaining a purified fermentation broth and/or adjusting pH of purified fermentation broth for avoiding during the subsequent evaporation of water the formation of vitamin C in a concentration higher than 2.5%, preferably not higher than 1% (based on dry substance), i) evaporating water from the purified fermentation broth for obtaining a concentrated purified fermentation broth, and j) recovering 2-keto-L-gulonic acid monohydrate crystals by crystallisation from the concentrated purified fermentation broth with a recovery yield for 2-keto-L-gulonic acid of 80% and higher.

The current invention relates to a process wherein in step g) filtration is microfiltration, in step h) said purified fermentation broth comprises not more tin 1800 ppm (measured as nitrogen on dry substance) proteins and adjusted pH is higher than 1.5, and in step j) recovery yield of 2-keto-L-gulonic acid is 85% or higher.

The current invention further relates to a process wherein in step b) the micro-organism is belonging to the genus *Gluconobacter* and in step e) the mixed culture of micro-organism is belonging to the genera *Gluconobacter* and *Bacillus*.

The current invention specifically relates to a process wherein in step e) the micro-organism is a mixed culture of *Gluconobacter oxydans*, preferably *Gluconobacter oxydans* SCB 329 deposited under Budapest Treaty at BCCM/LMG (Belgian Coordinated Collections of Micro-organisms/Bacteria Collection Laboratorium voor Microbiologie Universiteit Gent by Cerestar Holding B.V. Nijverheidsstraat 1, NL-4551 LA Sas van Gent, The Netherlands) on Apr. 24, 2001 under number LMG P-20356, and *Bacillus thuringiensis*, preferably *Bacillus thuringiensis* (SCB 933) TCV 393 deposited under Budapest Treaty at BCCM/LMG (Belgian Coordinated Collections of Micro-organisms/Bacteria Collection Laboratorium voor Microbiologie Universiteit Gent by Cerestar Holding B.V. Nijverheidsstraat 1, NL-4551 LA Sas van Gent, The Netherlands) on Apr. 24, 2001 under number LMG P-20355, and in said mixed culture the micro-organisms are present at the beginning of the growth in a ratio *Gluconobacter* colonies to *Bacillus* colonies between 300:1 and 1:10.

Furthermore, the current invention relates to a mixed culture of *Gluconobacter oxydans*, preferably *Gluconobacter oxydans* SCB 329 deposited at BCCM/LMG on Apr. 24, 2001 under number LMG P-20356, and *Bacillus thuringiensis*, preferably *Bacillus thuringiensis* (SCB 933) TCV 393 deposited at BCCM/LMG on Apr. 24, 2001 under number LMG P-20355 for producing 2-keto-L-gulonic acid.

Specifically the current invention relates to said mixed culture of micro-organisms wherein the micro-organisms are present at the beginning of the growth in a ratio of *Gluconobacter* colonies to *Bacillus* colonies of 25:1.

The current invention relates to a *Gluconobacter oxydans* SCB 329 deposited at BCCM/LMG on Apr. 24, 2001 under number LMG P-20356 for producing 2-keto-L-gulonic acid.

The current invention further relates to a *Bacillus thuringiensis* (SCB 933) TCV 393 deposited at BCCM/LMG on Apr. 24, 2001 under number LMG P-20355 for producing 2-keto-L-gulonic acid.

The current invention further relates to the use of micro-organism *Gluconobacter oxydans* SCB 329 deposited at BCCM/LMG on Apr. 24, 2001 under number LMG P-20356, and micro-organism *Bacillus thuringiensis* (SCB 933) TCV 393 deposited at BCCM/LMG on Apr. 24, 2001 under number LMG P-20355 for producing 2-keto-L-gulonic acid.

Finally the current invention relates to the use wherein said micro-organisms are applied in a mixed culture for producing 2-keto-L-gulonic acid.

DETAILED DESCRIPTION OF THE INVENTION

The present invention discloses a process for producing sodium 2-keto-L-gulonate by fermentation and recovering 2-keto-L-gulonic acid monohydrate crystals and said process comprises the following steps:

a) Fermentatively converting sorbitol into at least 50 g/L sodium 2-keto-L-gulonate, b) removing the micro-organisms from the fermentation medium thereby obtaining a micro-organism-reduced fermentation broth, preferably micro-organism-free fermentation broth, c) converting sodium 2-keto-L-gulonate into 2-keto-L-gulonic acid in the micro-organism-reduced fermentation broth, and removing proteins to a concentration below 2400 ppm (measured as nitrogen on dry substance) for obtaining a purified fermentation broth, and/or adjusting pH of purified fermentation broth for avoiding the formation of vitamin C at a concentration higher than 3% (based on dry substance) during the subsequent evaporation of water, d) evaporating water from the purified fermentation broth for obtaining a concentrated purified fermentation broth, and e) recovering 2-keto-L-gulonic acid monohydrate crystals by crystallisation from the concentrated purified fermentation broth with a recovery yield for 2-keto-L-gulonic acid of 80% or higher.

In order for recovering 2-keto-L-gulonic acid from the fermentation broth the fermentation broth is freed of micro-organisms and the produced sodium 2-keto-L-gulonate is converted into 2-keto-L-gulonic acid in the micro-organism free fermentation broth.

The recovery yield of 2-keto-L-gulonic acid strongly depends upon the purity of the micro-organism fermentation broth. In order for obtaining a recovery yield of 80% or higher for the 2-keto-L-gulonic acid, the current invention demonstrates a purification step, which comprises either one of two treatments that might be applied separately or which can be applied in sequence.

During the conversion of sodium 2-keto-L-gulonate into 2-keto-L-gulonic acid the residual proteins are removed to a concentration below 2400 ppm nitrogen (based on dry substance and measured with a Mitsubishi TN-05 analyser). Secondly, the pH of said purified micro-organism free fermentation broth is adjusted whereby the formation of vitamin C during the subsequent evaporation of water is avoided or its concentration is not higher than 4% (based on dry substance). Consequently, the high recovery yield for 2-keto-gulonic acid can be obtained by the removal of proteins and/or the adjustment of pH of the purified fermentation broth.

By removing the residual proteins to a concentration below 2400 ppm in the purified fermentation broth, the subsequent crystallisation step is facilitated due to the increased purity of the purified fermentation broth, and the reduced viscosity of that purified fermentation broth.

By adjusting the pH of said purified fermentation broth, the formation of vitamin C is avoided or its concentration is not higher than 3% and the concentrated purified fermentation broth has a higher purity thus facilitating the crystallisation and increasing the recovery yield.

Applying both treatments subsequently, i.e. removing the residual proteins and adjusting the pH of the purified fermentation broth has a cumulative effect and the recovery yield of 2-keto-L-gulonic acid is certainly higher than 80%.

The conversion of sodium 2-keto-L-gulonate into 2-keto-L-gulonic acid and the removal of proteins can be performed by applying ion exchange treatment consisting of a cation exchange ion. The ion exchange treatment is simplified and an anion exchanger is superfluous.

The positive effect of the purification treatment on the recovery yield of 2-keto-L-gulonic acid is independent from the fermentation process applied. The fermentation can be performed either batchwise or continuously.

The fermentation of sorbitol into sodium 2-keto-L-gulonate can be a one step fermentation, for example as it is described in EP 0 518 136, or the fermentative conversion can be a two-step continuous fermentation process such as is described in EP 0 972 843.

Specifically the current invention relates to a process comprising the following steps:
a) Preparing a fermentation culture medium containing a nitrogen-source and as carbon-source sorbitol,
b) Inoculating the fermentation culture medium with micro-organisms for converting sorbitol into L-sorbose,
c) Allowing the microorganisms to grow until at least 100 g/L L-sorbose is obtained in the fermentation medium,
d) Terminating the conversion of sorbitol into L-sorbose,
e) Inoculating the fermentation culture medium with a mixed culture of micro-organisms for converting L-sorbose into sodium 2-keto-L-gulonate,
f) Allowing the micro-organisms to grow until at least 50 g/L sodium 2-keto-L-gulonate is obtained in the fermentation medium,
g) removing the micro-organisms from the fermentation medium by filtration for obtaining a micro-organism-reduced fermentation broth, preferably a micro-organism-free fermentation broth,
h) converting with cation exchange resin sodium 2-keto-L-gulonate into 2-keto-L-gulonic acid in the micro-organism reduced fermentation broth, and removing proteins to a concentration below 2000 ppm proteins (measured as nitrogen on dry substance) for obtaining a purified fermentation broth and/or adjusting pH of purified fermentation broth for avoiding during the subsequent evaporation of water the formation of vitamin C in a concentration higher than 2.5%, preferably not higher than 1% (based on dry substance),
i) evaporating water from the purified fermentation broth for obtaining a concentrated purified fermentations broth, and
j) recovering 2-keto-L-gulonic acid monohydrate crystals by crystallisation from the concentrated purified-fermentation broth with a recovery yield for 2-keto-L-gulonic acid of 80% and higher.

The fermentative production of L-sorbose from D-sorbitol is known and that process is part of the well-known Reichstein process. Various Gluconobacter strains are known to produce L-sorbose from D-sorbitol.

This fermentation is continued until at least 100 g/L L-sorbose is obtained in the fermentation medium.

L-sorbose formation is analysed by HPLC (Ca-column).

Between the two fermentation steps, the fermentation broth can be pasteurised at a temperature higher than 50° C., preferably at a temperature higher than 80° C.

The conversion of L-sorbose into 2-keto-L-gulonic acid is characterised in that a mixed culture of micro-organisms *Gluconobacter oxydans* and *Bacillus thuringiensis*, is used more preferably a mixed culture of *Gluconobacter oxydans* SCB 329 deposited at BCCM/LMG on Apr. 24, 2001 under number LMG P-20356, and *Bacillus thuringiensis* (SCB 933) TCV 393 deposited at BCCM/LMG on Apr. 24, 2001 under number LMG P-20355.

The quantitative ratio in the mixed culture of *Gluconobacter* colonies to *Bacillus* colonies at the beginning of the growth may be in the range between 300:1 and 1:10, preferably in said mixed culture the micro-organisms are present at the beginning of the growth in a ratio *Gluconobacter* colonies to *Bacillus* colonies of 25:1.

The production of 2-keto-L-gulonic acid is effected by cultivating the mixed micro-organism culture in a medium containing L-sorbose as well as appropriate nutrients. Alternatively, the process may be carried out by culturing the mixed micro-organisms, thereafter, bringing the whole cells or a cell-free extract collected from the culture into contact with L-sorbose.

The fermentation temperature is between about 25° C. and 35° C.

The culture medium usually contains a carbon source, a nitrogen source, inorganic substances, vitamins, trace elements and other growth promoting factors.

Various organic or inorganic substances may be used as nitrogen source, such as yeast-extract, meat extract, peptone, casein, corn-steep liquor, amino acids, nitrates, urea, ammonium salts and the like. A inorganic substances, magnesium sulphate, potassium sulphate, ferrous and ferric chlorides, calcium carbon and the like may be used.

The fermentation process may be carried out at a pH between 5 and 8, preferably between about 6 and 8 and consequently, 2-keto-L-gulonic acid is produced as its corresponding salt, preferably sodium salt.

The micro-organisms are allowed to grow until at least 50 g/L sodium 2-keto-L-gulonate is obtained in the fermentation broth.

The process of the current invention describes a fermentative process wherein the micro-organisms are allowed to grow in a bubbled column or airlift reactor.

The formation of 2-keto-L-gluconic acid is analysed by HLPC (H$^+$-column).

The micro-organisms are removed from the fermentation broth for obtaining a micro-organism free fermentation broth. This separation step can be performed by filtration, preferably microfiltration.

Furthermore said process is characterised in that in step h) the purified fermentation broth is comprising not more than 1800 ppm (measured as nitrogen on dry substance) proteins and adjusted pH is higher than 1.5, whereas the recovery yield of 2-keto-L-gulonic acid is 85% or higher.

Specifically the treatment with cation exchange resin can be conducted such that the pH of the purified fermentation broth is not below 1.5. Either the micro-organism reduced or micro-organism free fermentation broth is fed to the cation exchange resin until the pH of the purified fermentation broth remains above 1.5 or treatment is continued until pH is dropping below 1.5 and subsequently, pH increased above 1.5 by adding alkali to the purified fermentation broth. The alkali can be any alkali metal hydroxide, alkali metal carbonate or bicarbonate and/or earth alkali metal carbonate or bicarbonate, preferably sodium hydroxide or potassium hydroxide.

In still another method, pH of the purified fermentation broth is adjusted above 1.5 by adding raw micro-organism reduced or micro-organism free fermentation broth to the purified fermentation broth. In order or avoiding the addition of 'foreign material' the raw (=non-purified micro-organism free fermentation broth) is added in an amount up to 10% of the total volume of the purified fermentation broth for adjusting the final pH above 1.5.

By adjusting pH of the purified fermentation broth, the formation of vitamin C during evaporation of water from the purified fermentation broth is completely avoided or the tendency for formation of vitamin C is reduced with at least 40% in comparison to a process without pH adjustment.

The concentration of vitamin C is not higher than 3%, preferably not higher than 2.5%, most preferably not higher than 1% (based on dry substance).

Reducing the concentration of residual proteins in the purified fermentation broth below 2400 ppm, preferably below 2000 ppm, more preferably below 1800 ppm can be obtained by operating the purification with the cation exchange resin such that the capacity of the resin controlled by the amount of bound nitrogen and to a lesser extent by the bound sodium ions. This method provides that sudden nitrogen increase only starts at the end of the sweetening off. All nitrogen bound to the column will stay in a very narrow band on the column and the residual amount of proteins in the purified fermentation broth is below 2400 ppm (measured as total nitrogen on dry substance with Mitsubishi TN-05 analyser). Controlling the capacity of the cation exchange resin by the bound sodium ions would increase the volume of the purified fermentation broth, but the purity in respect of residual proteins would be lower. Consequently, the latter method results in a lower recovery yield of the 2-keto-L-gulonic acid monohydrate crystals.

By applying the treatment of the current invention high recovery yields of 2-keto-L-gulonic acid can be achieved, higher than 80%, preferably at least 85%.

The current invention further relates to a mixed culture of *Gluconobacter oxydans*, preferably *Gluconobacter oxydans* SCB 329 deposited at BCCM/LMG on Apr. 24, 2001 under number LMG P-20356, and *Bacillus thuringiensis*, preferably *Bacillus thuringiensis* (SCB 933) TCV 393 deposited, at BCCM/LMG on Apr. 24, 2001 under number LMG P-20355 for producing 2-keto-L-gulonic acid.

Furthermore, in said mixed culture the micro-organisms are present at the beginning of the growth in a ratio *Gluconobacter* colonies to *Bacillus* colonies of 25:1.

The current invention relates to a *Gluconobacter oxydans* SCB 329 deposited at BCCM/LMG on Apr. 24, 2001 under number LMG P-20356 for producing 2-keto-L-gulonic acid.

The current invention further relates to a *Bacillus thuringiensis* (SCB 933) TCV 393 deposited at BCCM/LMG on Apr. 24, 2001 under number LMG P-20355 for producing 2-keto-L-gulonic acid.

The current invention further relates to the use of micro-organism *Gluconobacter oxydans* SCB 329 deposited at BCCM/LMG on Apr. 24, 2001 under number LMG P-20356, and micro-organism *Bacillus thuringiensis* (SCB 933) TCV 393 deposited at BCCM/LMG on Apr. 24, 2001 under number LMG P-20355 for producing 2-keto-L-gulonic acid.

Finally the current invention relates to the use wherein said micro-organisms are applied in a mixed culture for producing 2-keto-L-gulonic acid.

The current invention has the following advantages:
- high recovery yields of 2-keto-L-gulonic acid can be obtained even by running the fermentation in absence of calcium ions, thus resulting in a gypsum-free process,
- the micro-organisms are completely removed by microfiltration,
- the high recovery yields are obtainable by a single cation exchange resin treatment which allows complete conversion of sodium 2-keto-L-gulonate into 2-keto-L-gulonic acid and removal of residual proteins and/or the pH of the purified fermentation broth is adjusted for avoiding subsequent formation of vitamin C,
- the ion exchange treatment is simplified because the treatment with anion exchanger is superfluous,
- the obtained purity of said purified fermentation broth allows direct crystallisation of 2-keto-L-gulonic acid monohydrate from aqueous medium, with a high recovery yield of 80% or higher for 2-keto-L-gulonic acid,
- the process is completely free from the use of any organic solvent,
- the purity of the 2-keto-L-gulonic acid monohydrate crystals is at least 99.5%.
- the 2-keto-L-gulonic acid monohydrate can directly be employed for the conversions into vitamin C.

The current invention is illustrated by way of the following examples.

Example 1 describes the fermentation of D-sorbitol into L-sorbose.

Example 2 describes the second part of the fermentation, i.e conversion of L-sorbose into sodium 2-keto-L-gulonate.

Example 3 describes the cation exchange resin treatment wherein the content of residual proteins is brought below 2400 ppm nitrogen (measured with Mitsubishi TN-05 analyser) followed by the direct crystallisation.

Example 4 describes the caution exchange resin treatment and the adjustment of pH above 1.5 by adding raw micro-organism free fermentation broth, for avoiding the formation of vitamin C.

Example 5 describes pH adjustment by adding NaOH.

Example 6 and 7 are comparative examples demonstrating that the recovery yield is lower when the content of residual proteins is above 2400 ppm, and formation of vitamin C when pH of eluent is not adjusted, respectively.

EXAMPLES

Example 1

Fermentation of D-Sorbitol into L-Sorbose

*Gluconobacter oxydans* NRRL B72 was cultivated at 28° C. for 2 days in a Roux flask containing 75 mL of a medium composed of 50 g/L D-sorbitol (Cerestar C☆16122), 3.75 g/L (ds) corn steep liquor, 0.45 g/L $(NH_4)_2SO_4$, 0.11 g/L $(NH_4)_2HPO_4$, 0.08 g/L $MgSO_4.7H_2O$, 1.0 g/L calcium acetate monohydrate and 20 g/L agar. The pH was adjusted to 5.0 with concentrated acetic acid before sterilisation.

Cells were recovered in 50 mL of a 0.9% NaCl solution and inoculated into a 2 L fermenter containing 1.35 L of a culture medium composed of 100 g/L D-sorbitol (Cerestar C✫16122), 3.75 g/L (ds) corn steep liquor, 0.45 g/L (N$_2$SO$_4$, 0.11 g/L (NH$_4$)$_2$HPO$_4$, 0.08 g/L MgSO$_4$.7H$_2$O, 1.0 g/L calcium acetate monohydrate and 100 ppm antifoam.

After 24 h cultivation at 32° C., 1.0 VVM and 700 RPM, 300 mL of the culture were inoculated into a 20 L fermenter containing 13.7 L of a medium composed of 230 g/L D-sorbitol (Cerestar C✫16122), 5.25 g/L (ds) corn steep liquor, 0.45 g/L (NH$_4$)$_2$SO$_4$, 0.11 g/L (N$_4$)$_2$HPO$_4$, 0.08 g/L MgSO$_4$.7H$_2$O, 1.0 g/L calcium acetate monohydrate and 100 ppm antifoam. After sterilisation the pH was adjusted to 5.0–5.2 by using 40% (w/v) sodium hydroxide. The fermentation was continued at 35° C. and 0.5 VVM until total consumption of the initial sorbitol. The pO$_2$ was controlled at 50% by RPM variation (during the maximum conversion phase, the pO$_2$ however dropped below 50%).

Twenty one hours were needed to convert the initial sorbitol, with a weight yield of 96%. At the end of the sorbitol to L-sorbose conversion, a pasteurisation treatment was applied to inactivate the biomass (60° C. for 2 hours).

Example 2

Fermentation of L-Sorbose into Sodium 2-keto-L-gulonate

*Gluconobacter oxydans* SCB 329 deposited at BCCM/LMG on Apr. 24, 2001 under number LMG P-20356' was cultivated in a Roux flask containing 75 mL of a medium composed of 10.0 g/L crystaline L-sorbose, 2.0 g/L crystaline glucose, 5.0 g/L yeast extract, 5.0 g/L rice peptone, 0.5 g/L KH$_2$PO$_4$, 0.2 g/L MgSO$_4$.7H$_2$O, 20 g/L MOPS (3-N-morpholino-propanesulphonic acid) and 20 g/L agar. The pH value of the medium was adjusted to 7.5 before sterilisation. After 24 h cultivation at 28° C., *Bacillus thuringiensis* (SCB 933) TCV 393 deposited at BCCM/LMG on Apr. 24, 2001 under number LMG P-20355 was inoculated on the same flask by making 2 longitudinal strikes. Incubation was continued for 24 hours at 28° C.

A ratio *Gluconobacter oxydans* to *Bacillus thurigiensis* of 25 to 1 was obtained.

*Gluconobacter oxydans* and *Bacillus thurigiensis* were recovered in 50 mL of a NaCl solution and inoculated into a baffled flask containing 0.7 L of a culture medium composed of 15.0 g/L crystaline L-sorbose, 2.0 g/L glucose, 1.5 g/L (ds) corn steep liquor, 5.0 g/L yeast extract, 5.0 g/L rice peptone, 4.0 g/L urea, 5.0 g/L KH$_2$PO$_4$, 0.2 g/L MgSO$_4$.7H$_2$O and 4.0 g/L calcium carbonate. L-sorbose and glucose were sterilised separately. The pH value of the proteins and salts mixture was adjusted before sterilisation to obtain 6.8 after sterilisation. The seed culture (1) was incubated at 28° C. with 150 RPM transversal shaking for 24 h.

28 mL of the seed culture were transferred to a 2 L fermenter containing 1.4 L of the same medium as described above plus 0.3 g/L silicon-based antifoam. The fermenter was run at 28° C., 0.7 VVM and 850 RPM for 14 hours for obtaining seed culture 2.

140 mL of this seed culture 2 was inoculated into a second 2 L fermenter containing 1.26 mL of a medium composed of 30 g/L sorbitol, 2.0 g/L glucose, 14.0 g/L (ds) corn steep liquor, 5.0 g/L yeast extract, 0.5 g/L KH$_2$PO$_4$, 0.1 g/L MgSO$_4$, 0.2 g/L silicon-based antifoam at pH 6.8 (adjusted by addition of sodium hydroxide after sterilisation). This seed culture 3 was cultivated at 28° C., 0.7 VVM, 850 RPM for 14 h. The pH was maintained at 6.8 by addition of sodium hydroxide.

After 14 h culture, 84 mL of the seed culture 3 was transferred into a 2 L fermenter containing 1.316 mL of the same medium as used in the seed culture 3, except that yeast extract concentration was increased up to 10.0 g/L. Cultivation parameters were also identical to the seed culture 3, and seed culture 4 was obtained.

0.7 L of seed culture 4 was inoculated into a 20 L production fermenter containing 10.5 L of a medium composed of 890 g of pasteurised sorbose (obtained in example 1), 168 g (ds) corn steep liquor, 3.1 g yeast extract, 7.0 g KH$_2$PO$_4$, 1.4 g MgSO$_4$.7H$_2$O and 4.2 g silicon-based antifoam. L-sorbose was added in a sterile way to the sterile proteins and salts mixture. The pH value of the medium was adjusted to 7.0 before inoculation Aeration was maintained at 0.5 VVM and pO$_2$ controlled at 40% by RPM variation. The pH was maintained at 7.0 by addition of sodium hydroxide. Foam formation was controlled using a 10% solution of silicon-based antifoam. After 12 h of fermentation, 580 g of pasteurised L-sorbose was added in a sterile way. Thirty six hours were needed to reach a residual L-sorbose concentration lower than 1 g/L and 96% (weight yield) 2-keto-L-gulonic acid was obtained.

Example 3

Purification with Cation Exchange Resin—Crystallisation

1) Cation Exchange Treatment 41.2 kg Micro-organism free fermentation broth (=filtrate of microfiltration) at 12.4% d.s. was passed over a column containing 17 L strong cation exchange resin (Lewatit® S2528). 50.3 kg of purified micro-organism free fermentation broth at 8.8% d.s. were obtained.

This solution was analysed for N content on a Mitsubishi TN-05 analyser.

The obtained results are displayed in Table 1.

TABLE 1

|  | Filtrate | Purified |
| --- | --- | --- |
| d.s.(%) | 12.4 | 8.8 |
| Density(kg/l) | 1.066 | 1.042 |
| KGA (% on ds) | 82.5 | 82.5 |
| N ppm on ds | 4100 | 1800 |
| pH | 5.7 | 1.5 |

2) Crystallisation 39.1 kg purified micro-organism free fermentation broth was concentrated at reduced pressure to a concentration of 62.5% d.s.

5.5 kg of this concentrated liquor were transferred to a batch cooling crystalliser. Cooling program was as follows: in 1 hour from 60° C. to 50° C., subsequently in 3 hours from 50° C. to 25° C.

At the end of the cooling cycle the massecuite was quantitatively transferred to a batch lab centrifuge operating at 1750 g-force and 1705 g 2-keto-L-gulonic acid monohydrate crystals were recovered with a purity of 99.2% and total moisture content of 10%.

The remaining mother liquor having a purity of 68% was concentrated to 71% d.s.

2665 g concentrated liquor was transferred to a cooling crystalliser and the same temperature profile as for the first crystallisation was applied.

Centrifugation of the massecuite resulted in another 990 g crystals with a purity of 98.9% and a moisture content of 11%.

An overall recovery of 85% 2-keto-L-gulonic acid was obtained.

Example 4 pH Adjustment by Adding Raw Micro-Organism Free Fermentation Broth 47 kg of filtrate of microfiltration (pH=1.5, d.s.=8%) with a vitamin C content of 0.54% (based on d.s.) was mixed with 5 L of raw (not-purified) micro-organism free fermentation broth (pH=5.3 d.s=11.2%, Vitamin C=0.44% on d.s.). The obtained mixture had a pH of 1.83; the content of vitamin C was 0.53% (based on ds) and the total dry substance was 8.7%.

This mixture was concentrated in a small 20 L vacuum pan to a final volume of 6.3 kg at a dry substance of 60.8%. The liquor temperature during concentration was around 50° C. and towards the end the temperature increased to 60° C.–65° C.

At the end of the concentration step the final vitamin C content was 0.97% (based on dry substance).

This concentrated liquor was transferred to a cooling crystalliser which was operated with the following temperature profile: main the temperature 60° C. for 3 hour, cooling from 60° C. to 45° C. in 2 hours and in 12 hours from 45° C. to 10° C.

At the end of the crystallisation cycle the concentrated purified micro-organism free fermentation broth had a vitamin C content of 2.37% based on dry substance.

Example 5

With pH Adjustment by Adding NaOH

To 31900 g of filtrate of microfiltration (pH=127, ds=12.8%,) 150 g of NaOH solution at 31% was added. The pH increased to 1.35. It was then concentrated in a rotative evaporator under vacuum to 7000 g at 60% ds. The liquor temperature during evaporation was around 50° C. and increased towards the end to 60° C.–65° C. Vit C content at the end of evaporation was 2.6% on ds.

This liquor was transferred to a cooling crystalliser were 1 g of seed was added and operated as follows: maintaining at 60° C. over 3 hour to reduce supersaturation, cooling from 60° C. to 45° C. in 2 hours and from 45° C. to 10° C. in 12 hours.

The massecuite was centrifuged and 1950 g crystals of 2-keto-L-gulonic acid at 10.5% moisture with purity of 99.8% were obtained.

The residual mother liquors were concentrated and crystallised as above in two other consecutive steps leading to resp 610 g at 9.9% moisture and 99.3% purity and 477 g crystals at 10.7% moisture and 96.5% purity of 2-keto-L-gulonic acid.

This resulted in a total recovery yield of 85.3%.

Example 6 (Comparative)

Cation Exchange Resin—Crystallisation

1) Cation Exchange Treatment—N-Content not Below 2400 ppm (on d.s.)

47.8 kg filtrate of microfiltration (=equivalent to 2.7 bedvolumes) was passed over 17 L strong cation exchange resin (Lewatit® S2528). 57.7 kg purified micro-organism free fermentation broth at 8.9% ds was obtained with a N-content of 2400 ppm on d.s. (measured with Mitsubishi analyser TN-05).

The obtained results are displayed in Table 2.

TABLE 2

|  | Filtrate | Purified |
|---|---|---|
| d.s.(%) | 12.4 | 8.9 |
| Density(kg/l) | 1.066 | 1.042 |
| KGA % | 82.5 | 82.5 |
| N ppm on ds | 4100 | 2400 |
| pH | 5.7 | 1.5 |

2) Crystallisation 39.1 g of the purified micro-organism free fermentation broth was concentrated at reduced pressure to 62.5% ds.

5.5 kg of this concentrated liquor was transferred to a batch cooling crystalliser. The following cooling program was used: from 60° C. to 50° C. in 1 hour, from 50° C. to 25° C. in 3 hour.

At the end of the cooling cycle the massecuite was quantitatively transferred to a batch lab centrifuge operating at 1750 g-force and 1690 g crystals were recovered as 2-keto-L-gulonic, acid monohydrate at a purity of 99.2% and total moisture content of 10%.

The remaining mother liquor had a purity of 67.5% and was concentrated to 71% d.s. 2700 g concentrated liquor was transferred to a cooling crystalliser and the same temperature profile as for the first crystallisation was applied.

The centrifugation of this massecuite gave difficulties in the separation of the mother liquor from the crystals. Due to the higher protein content the viscosity of the suspension was increased. Therefore, the suspension had to be diluted to be able to recover the crystals.

Centrifugation of the diluted massecuite resulted in 820 g crystals with a purity of 98.9% and a moisture content of 11%.

An overall recovery of 79% for 2-keto-l-gulonic acid was obtained

Example 7

Without pH Adjustment 31900 g of filtrate of microfiltration (pH=1.27, ds=12.8%,) with a Vit C content of 1.68% on ds was concentrated in a rotative evaporator under vacuum to 7000 g at 57.5% ds. The liquor temperature during evaporation was around 50° C. and increased towards the end to 60° C.–65° C. Vit C content at the end of evaporation was 3.1% on ds. This liquor was transferred to a cooling crystalliser were 1 g of seed was added and operated as follows: maintaining at 60° C. over 3 hour to reduce supersaturation, cooling from 60° C. to 45° C. in 2 hours and from 45° C. to 10° C. in 12 hours.

The massecuite was centrifuged and the mother liquor was also analysed for Vit C; the content was 5.9% on ds. 1740 g crystals of 2-keto-1-gulonic acid at 10:6% moisture and purity of 99.8% were recovered.

The residual mother liquors were concentrated and crystallised as above in two other consecutive steps leading to a crystal mass of resp 714 g crystals at 9.8% moisture and purity of 99.3% and 355 g crystals at 10% moisture and 97.7% purity.

This resulted in a total recovery yield of 79%. Vit C content of the final mother liquor was 14% on ds.

The invention claimed is:

1. A process for producing sodium 2-keto-L-gulonate by fermentation and recovering 2-keto-L-gulonic acid monohydrate crystals, said process comprising:
   a) fermenting sorbitol in a fermenting medium in the presence of micro-organisms for converting sorbitol into at least 50 g/L sodium 2-keto-L-gulonate,
   b) removing the microorganisms from the fermentation medium thereby obtaining a microorganism-reduced fermentation broth,
   c) converting sodium 2-keto-L-gulonate into 2-keto-L-gulonic acid in the microorganism-reduced fermentation broth, and removing proteins to a concentration below 2400 ppm measured as nitrogen on dry substance to obtain a purified fermentation broth and adjusting the pH of the purified fermentation broth to a pH above 1.5 for avoiding the formation of vitamin C in a concentration higher than 3% based on dry substance, during the subsequent evaporation of water,
   d) evaporating water from the purified fermentation broth to obtain a concentrated purified fermentation broth, and
   e) recovering 2-keto-L-gulonic acid monohydrate crystals by crystallization from the concentrated purified fermentation broth with a recovery yield for 2-keto-L-gulonic acid of 80% or higher.

2. The process according to claim 1 wherein in the step c) of said process the conversion into 2-keto-L-gulonic acid and the removal of proteins is obtained by ion exchange treatment consisting of cation exchange resin.

3. The process for producing sodium 2-keto-L-gulonate by fermentation and recovering 2-keto-L-gulonic acid monohydrate crystals, said process comprising:
   a) preparing a fermentation culture medium containing a nitrogen-source and as a carbon source sorbitol,
   b) inoculating the fermentation culture medium with microorganisms for converting sorbitol into L-sorbose,
   c) allowing the microorganisms to grow until at least 100 g/L L-sorbose is obtained in the fermentation medium,
   d) terminating the conversion of sorbitol into L-sorbose,
   e) inoculating the fermentation culture medium with microorganisms for converting L-sorbose into sodium 2-keto-L-gulonate,
   f) allowing the micro-organisms to grow until at least 50 g/L sodium 2-keto-L-gulonate is obtained in the fermentation medium,
   g) removing the microorganisms from the fermentation medium by filtration for obtaining a micro-organism-reduced fermentation broth,
   h) converting with cation exchange resin sodium 2-keto-L-gulonate into 2-keto-L-gulonic acid in the microorganism-reduced fermentation broth, and removing proteins to a concentration below 2000 ppm measured as nitrogen on dry substance and obtaining a purified fermentation broth and adjusting the pH of the purified fermentation broth to a pH above 1.5 for avoiding the formation of vitamin C in a concentration higher than 2.5% based on dry substance, during the subsequent evaporation of water,
   i) evaporating water from the purified fermentation broth to obtain a concentrated purified fermentation broth, and
   j) recovering 2-keto-L-gulonic acid monohydrate crystals by crystallization from the concentrated purified fermentation broth with a recovery yield for 2-keto-L-gulonic acid of 80% and higher.

4. The process according to claim 3 wherein in step g) filtration is microfiltration, in step h) said purified fermentation broth comprises not more than 1800 ppm measured as nitrogen on dry substance proteins and adjusted pH is higher than 1.5, and
   in step j) recovery yield of 2-keto-L-gulonic acid is 85% or higher.

5. The process according to claims 3 or 4 wherein in step e) the microorganism is a mixed culture of *Gluconobacter oxydans*, and *Bacillus thuringiensis*, and in said mixed culture the microorganisms are present at the beginning of the growth in a ratio of Gluconobacter colonies to Bacillus colonies between 300:1 and 1:10.

6. The process according to claim 1, wherein in step b) said fermentation broth is a microorganism free fermentation broth.

7. The process according to claim 3, wherein in step g) said fermentation broth is a microorganism free fermentation broth.

8. The process according to claim 3, wherein in step h), the concentration of vitamin C is not higher than 1% (based on dry substance).

9. The process according to claim 5, wherein said *Gluconobacter oxydans* comprises *Gluconobacter oxydans* SCB 329 deposited at BCCM/LMG on 24/04/2001 under number LMG P-20356, and said *Bacillus thuringiensis* comprises *Bacillus thuringiensis* (SCB 933) TCV 393 deposited at BCCM/LMG on 24/04/2001 under number LMG P-20355.

10. The process according to claim 1, wherein in c), the pH of the purified fermentation broth is adjusted to a pH above 1.5 by adding microorganism-free fermentation broth or additional microorganism-reduced fermentation broth to the purified fermentation broth.

11. A process for producing sodium 2-keto-L-gulonate by fermentation and recovering 2-keto-L-gulonic acid monohydrate crystals, said process comprising:
    a) fermenting sorbitol in a fermenting medium in the presence of micro-organisms for converting sorbitol into at least 50 g/L sodium 2-keto-L-gulonate,
    b) removing the microorganisms from the fermentation medium thereby obtaining a microorganism-reduced fermentation broth,
    c) converting sodium 2-keto-L-gulonate into 2-keto-L-gulonic acid in the microorganism-reduced fermentation broth, and removing proteins to a concentration below 2400 ppm measured as nitrogen on dry substance to obtain a purified fermentation broth and adding sufficient amount of a base to adjust the pH of the purified fermentation broth to a pH above 1.5 for avoiding the formation of vitamin C in a concentration higher than 3% based on dry substance, during the evaporating step,
    d) evaporating water from the purified fermentation broth to obtain a concentrated purified fermentation broth, and
    e) recovering 2-keto-L-gulonic acid monohydrate crystals by crystallization from the concentrated purified fermentation broth with a recovery yield for 2-keto-L-gulonic acid of 80% or higher.

12. The process according to claim 10, wherein in c) said base comprises at least one of an alkali metal hydroxide, an alkali metal carbonate, an alkali metal bicarbonate, alkaline earth metal carbonate, or an alkaline earth metal bicarbonate.

* * * * *